US00PP14371P29

(12) United States Plant Patent
Unger

(10) Patent No.: US PP14,371 P2
(45) Date of Patent: Dec. 16, 2003

(54) THUNBERGIA PLANT NAMED 'LEMON STAR'

(50) Latin Name: *Thunbergia alata*
Varietal Denomination: Lemon Star

(75) Inventor: Michael H. Unger, Rheinfelden (DE)

(73) Assignee: Unger Breeding, Rheinfelden (DE)

( * ) Notice: Subject to any disclaimer, the term of this patent is extended or adjusted under 35 U.S.C. 154(b) by 0 days.

(21) Appl. No.: 10/113,594

(22) Filed: Apr. 1, 2002

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Susan B. McCormick
(74) *Attorney, Agent, or Firm*—Wood, Phillips, Katz, Clark & Mortimer

(57) ABSTRACT

A new and distinct Thunbergia plant named 'Lemon Star', characterized by its bright yellow flowers, dark green leaves, good basal branching character and climbing, spreading growth habit.

2 Drawing Sheets

Latin name of the genus and species of plant claimed: *Thunbergia alata.*
Variety denomination: 'Lemon Star'.

BACKGROUND OF THE INVENTION

The present invention comprises a new and distinct Thunbergia plant, botanically known as *Thunbergia alata,* and hereinafter referred to by the cultivar name 'Lemon Star'.

The new Thunbergia resulted from an induced chemical mutation of the seed variety *Thunbergia alata* (not patented). The 'Lemon Star' cultivar was discovered and selected by the inventor in 1999, at Rheinfelden, Germany. 'Lemon Star' is vegetatively reproduced rather than produced from seed, is more vigorous and has darker flower color than the parent.

Asexual reproduction of the new cultivar by terminal tip cuttings has demonstrated that the characteristics of the new cultivar as herein described are firmly fixed and retained through successive generations of such asexual propagation.

SUMMARY OF THE INVENTION

It was found that the cultivar of the present invention:

(a) exhibits bright yellow flowers;

(b) forms dark green foliage;

(c) exhibits a good branching character; and (d) exhibits a vigorous climbing and trailing growth habit.

The new cultivar of the present invention can be compared to 'Susie Yellow' (not patented). In side by side comparisons, plants of the new cultivar exhibit a more vigorous growth habit, larger leaves and brighter yellow flowers than those of 'Susie Yellow'.

BREIF DESCRIPTION OF PHOTOGRAPH

The accompanying photographs show as nearly true as it is reasonably possible to make the same in color illustrations of this type, typical flower and foliage characteristics of the new cultivar. The plants were grown for 14 weeks in a greenhouse at West Chicago, Ill.

FIG. 1 illustrates the general plant from and growth habit of 'Lemon Star'.

FIG. 2 illustrates a close up of the flowers of 'Lemon Star'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Aug. 15, 2001. The readings were taken between 1:00 and 3:00 p.m. under natural daylight conditions. The plants were produced from cuttings taken from stock plants and were grown in a double poly carbonate covered greenhouse under conditions comparable to those used in commercial practice while utilizing a soilless growth medium. Temperatures of approximately 70° to 80° F. (21° to 26° C.) during the day and approximately 60° to 65° F. (15° to 18° C.) during the night and light levels between 5,000 and 8,000 were maintained. Plants used for the following descriptions and measurements were grown for 14 weeks from rooted cuttings.

Classification:
*Botanical.*—*Thunbergia alata* cultibar 'Lemon Star'.
Propagation:
*Type cutting.*—Terminal tip.
*Time to initiate roots.*—Approximately 7–10 days.
*Time to develop roots.*—Approximately 21 to 30 days.
*Root description.*—Fibrous, branching.
Plant description:
*Form.*—Climbing and trailing.
*Habit of growth.*—Vigorous. Pinching improves basal branching. A mature plant, 14 weeks after the plating of a rooted cutting, commonly has an average of 4.2 basal branches.
*Branches.*—Wiry. Up to 149.8 cm long and 1 mm in diameter. Texture: Moderately to densely pubescent. Color: 144B with slight overlay of 187B. Length of longest internode: Approximately 12.7 cm.

*Foliage.*—Leaves are non-fragrant, simple, opposite, at an acute angle to the stem, triangular to ovate, with dentate margin, acute apex and sagittate base. Upper and lower surfaces are densely pubescent. Leaf length is approximately 4.4 cm and width is approximately 3.9 cm. Upper surface is 146B, lower surface is between 147B and 147C. Both upper and lower surfaces have 5 nerved, palmate venation. Venation of upper surface is 146A. Venation of lower surface is 147C. Petiole length is approximately 3 cm, diameter, including wings, is approximately 3 cm. Texture: Very sparsely pubescent. Petiole color: Closest to 144C. Wing color:144A.

*Flowering description:*

*Flowering habit.*—Freely flowering.

*Natural flowering season.*—Year round in greenhouse environment; spring through autumn in outdoor garden.

*Flower type.*—Solitary, axillary, slaverform. Flowers are persistent.

*Peduncle.*—Strong, densely pubescent with acute angle, approximately 5.5 cm in length, less than 1 mm in diameter and 144C.

*Bud.*—Ovate, approximately 2.5 cm in length, 1.3 cm in diameter. Bud, just before opening, is 11C.

*Flower description.*—Non-Fragrant. Composed of five (5) petals fused at base to form corolla tube. Corolla is round and aspect is flat. Diameter is approximately 5 cm. Sepals — Number: 2. Length: Approximately 2.5 cm. Width: At base approximately 1.5 cm tapering to an acuminate tip. Texture: Outer surface is densely pubescent, inner surface is glabrous. Color: Outer surface is 138A, inner surface is 138B. Petals are non imbricate, have sunken apices and entire margin. Petal size: Approximately 2 cm long from throat and 1.8 cm wide. Color of upper surface when fully opened is 9A. Color of lower surface when fully opened is 11C. Corolla tube diameter: At throat it is approximately 9 mm in diameter and at base it is 3 mm in diameter. Corolla tube length: Approximately 2.9 cm. Throat texture: Upper ¼ is pubescent, rest is smooth. Throat color: 187B. Color of outer surface of corolla tube is 11C near opening and 79C at base.

*Calyx.*—Approximately 5 mm in length. The outer surface is densely pubescent and 149D.

*Bracts.*—Number: Approximately 10. Length: Approximately 2.9 cm. Width: Approximately 1.7 cm. Color: 145B with venation of 187A.

*Reproductive organs.*—Androecium: There are 4 stamens. Anther size: 4 mm in length.

Anther color: 2D. Pollen was not observed. Gynoecium: One pistil. Stigma length: 3 mm. Stigma color: 2D. Stigma texture: Smooth. Style length: 1.3 cm. Style color: 2D. Ovary diameter: 2 mm. Ovary color: 144B.

Seed production: Seed production has not been observed.

Disease resistance: Resistance to pathogens common to Thunbergia has not been observed.

I claim:

1. A new and distinct cultivar of Thunbergia plant named 'Lemon Star' substantially as herein shown and described, which:

(a) exhibits bright yellow flowers;

(b) forms dark green foliage;

(c) exhibits a good basal branching character; and (d) exhibits a vigorous climbing and spreading growth habit.

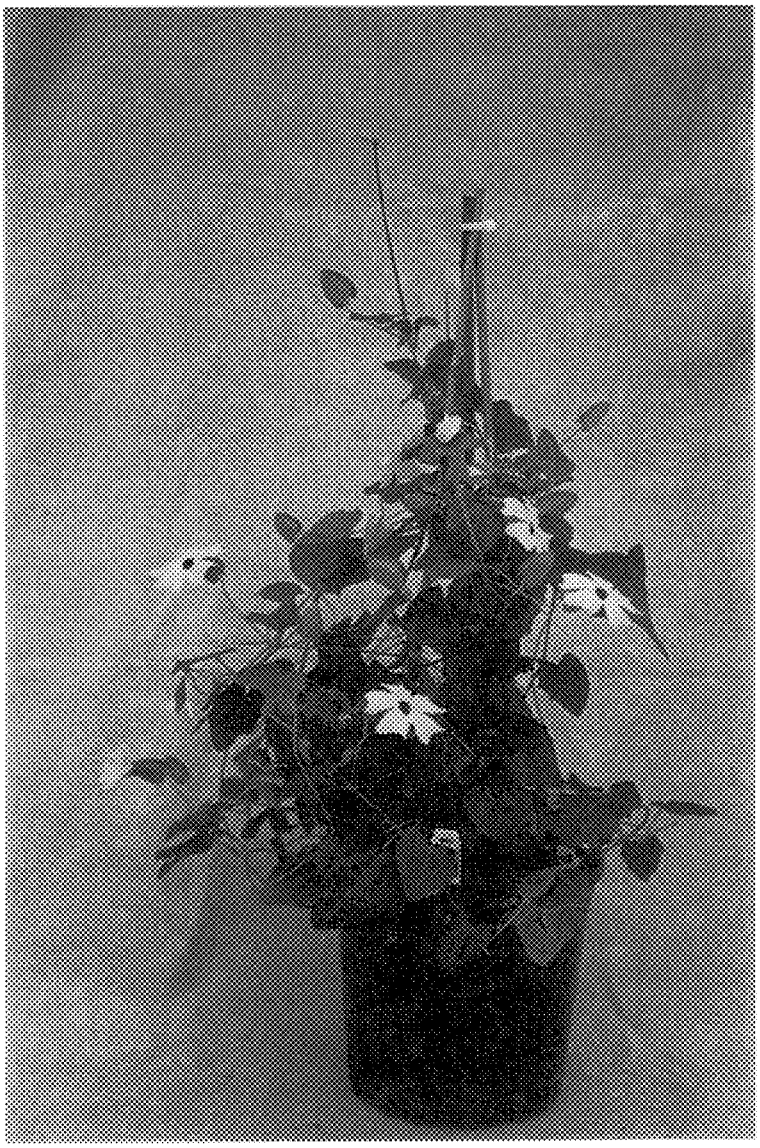

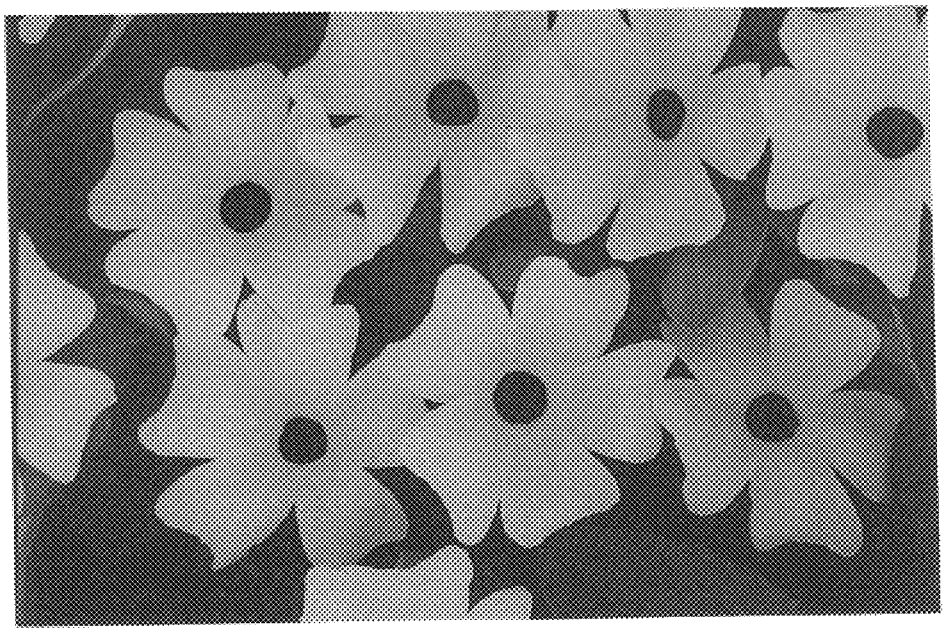

* * * * *